(12) United States Patent  
Body

(10) Patent No.: US 9,134,322 B2  
(45) Date of Patent: Sep. 15, 2015

(54) COMBINATION FOR EARLY EXCLUSION OF ACUTE MYOCARDIAL INFARCTION

(76) Inventor: Richard Body, Manchester (GB)

(\*) Notice: Subject to any disclaimer, the term of this patent is extended or adjusted under 35 U.S.C. 154(b) by 180 days.

(21) Appl. No.: 13/528,304

(22) Filed: Jun. 20, 2012

(65) Prior Publication Data

US 2013/0345581 A1  Dec. 26, 2013

(51) Int. Cl.
*A61N 1/00* (2006.01)
*G01N 33/68* (2006.01)
*A61B 5/0402* (2006.01)
*A61B 5/0472* (2006.01)

(52) U.S. Cl.
CPC .......... *G01N 33/6887* (2013.01); *A61B 5/0402* (2013.01); *A61B 5/0472* (2013.01); *G01N 33/6893* (2013.01); *G01N 2333/4703* (2013.01); *G01N 2800/324* (2013.01); *G01N 2800/56* (2013.01)

(58) Field of Classification Search
CPC ..................................................... A61B 5/0452
USPC .......................................... 600/513, 515, 518
See application file for complete search history.

(56) References Cited

U.S. PATENT DOCUMENTS

2008/0228094 A1\* 9/2008 Audet et al. .................. 600/513
2012/0264138 A1\* 10/2012 Hess et al. ..................... 435/7.4

\* cited by examiner

*Primary Examiner* — Nicole F Lavert
*Assistant Examiner* — Nadia A Mahmood
(74) *Attorney, Agent, or Firm* — Cesari and McKenna, LLP

(57) ABSTRACT

A method for 'ruling out' acute myocardial infarction (AMI) in a subject presenting with chest pain expected to be cardiac in nature. The method includes a) recording an Electrocardiography (ECG) reading from said subject, b) determining the amount of Heart-type Fatty acid binding protein (H-FABP) and cardiac Troponin T (cTnT) in a sample from said subject, c) comparing the results from b) to reference values for ruling out an acute Myocardial Infarction in a subject, and d) based on the results from steps a)-c) either 'ruling out' or 'ruling in' a diagnosis of acute Myocardial Infarction in said subject.

12 Claims, 3 Drawing Sheets

COMBINATION FOR EARLY EXCLUSION OF ACUTE MYOCARDIAL INFARCTION

BACKGROUND TO THE INVENTION

The search for an effective strategy that would help clinicians to exclude the diagnosis of acute myocardial infarction (AMI) without the need for serial troponin testing over a number of hours has been ongoing for many years. High sensitivity troponin (hs-Tn) assays, which have greater analytical sensitivity and precision than standard assays, have been shown to improve sensitivity for AMI when measured at the time of initial presentation (1-3). However, while the negative predictive value is improved at the time of presentation, even hs-Tn cannot exclude AMI without serial sampling. Studies have also shown that hs-Tn assays can detect cardiac troponin in patients with stable heart disease who have not suffered an acute event.

As troponin is a 'late marker' of myocardial necrosis (blood levels may take several hours to increase significantly), there has been significant interest in using so-called 'early markers' of myocardial necrosis to exclude AMI during the period of 'troponin blindness'. The most extensively investigated strategy involves 'triple marker testing' for troponin, creatine kinase MB fraction (CK-MB) and myoglobin (4). A recent multinational study suggested that this strategy may help to exclude AMI in less than 10% of patients, even with serial sampling over 2 hours (5). The strategy relies on selection of a very low risk patient group through clinical risk scoring as the biomarker panel has a sensitivity of only 82.1%. Additional work has demonstrated that this strategy is not cost-effective (6, 7).

Heart fatty acid binding protein (H-FABP) is contained within the cytoplasm of cardiac myocytes and has shown promise as an alternative 'early marker' of AMI. Compared to standard troponin assays, H-FABP has superior sensitivity for AMI in patients who present early (<4 h) after symptom onset (8). H-FABP and troponin (using standard assays) are independent predictors of prognosis (9). It has previously been demonstrated that the combination of troponin (using a standard assay) and H-FABP is unequivocally superior to triple marker testing for early diagnosis at the time of presentation to the ED (10). However, it is not known whether H-FABP adds incremental diagnostic value when high sensitivity troponin assays are used.

The electrocardiograph (ECG) is a commonly used diagnostic tool in cases of suspected myocardial infarction. It records the rhythm and electrical activity of the heart and can indicate abnormalities. However the ECG can appear normal in cases of ischemia or infarction and therefore in isolation it cannot rule out AMI.

There remains a clinical need for a strategy to better enable diagnosis when a patient presents with chest pain. A quick and accurate diagnosis means patients requiring treatment can be administered to immediately and those who don't can be reassured and released. As described herein the current invention enables a method to improve diagnosis of AMI and help predict future risk of a major adverse cardiac event (MACE).

REFERENCES

1. Reichlin, T. et al. (2009) *New England Journal of Medicine;* 361:858-67.
2. Keller, T. et al. (2010) *Journal of the American College of Cardiology;* 55:2096-106.
3. Januzzi, J. L. Jr. et al. (2010) *Circulation;* 121:1227-34.
4. McCord, J. et al. (2001) *Circulation;* 104:1483-8.
5. Than, M. et al. (2011) *Lancet;* 377:1077-84.
6. Goodacre, S. et al. (2010) *Heart*; Online first, doi: 10.1136/hrt.2010.203166.
7. Fitzgerald, P, et al. (2011) *Academic Emergency Medicine*, Ref Type: In Press
8. McCann, C, et al. (2008) *European Heart Journal;* 29:2843-50.
9. Kilcullen, N, et al. (2007) *Journal of the American College of Cardiology;* 50:2061-7.
10. Body, R. et al. (2011) *Resuscitation*; Online first, doi: 10.1016/j.resuscitation.2011.03.015.
11. Body, R. et al. (2011) *Clinica Chimica Acta;* 412:614-8.
12. Body, R. et al. (2010) *Resuscitation;* 81:281-6.
13. Body, R. et al. (2009) *Emergency Medicine Journal;* 27:292-6.
14. Body, R. et al. (2009) *Clinica Chimica Acta;* 404:89-94.
15. Body, R. et al. (2009) *Emergency Medicine Journal;* 26:95-9.
16. Body, R. et al. (2008) *Resuscitation;* 79:41-5.
17. Body, R. et al. (2011) *Journal of the American College of Cardiology;* 58:1333-9.

SUMMARY OF THE INVENTION

The current invention demonstrates that H-FABP and hs-TnT have independent diagnostic value for AMI and that the combination of H-FABP, hs-TnT and an ECG could be useful in a clinical scenario to 'rule out' AMI at the time of initial presentation without the need for serial sampling. This investigative combination also allows remaining patients to be stratified into risk groups for a MACE occurring within the next 30 days.

DETAILED DESCRIPTION

Figure 1:
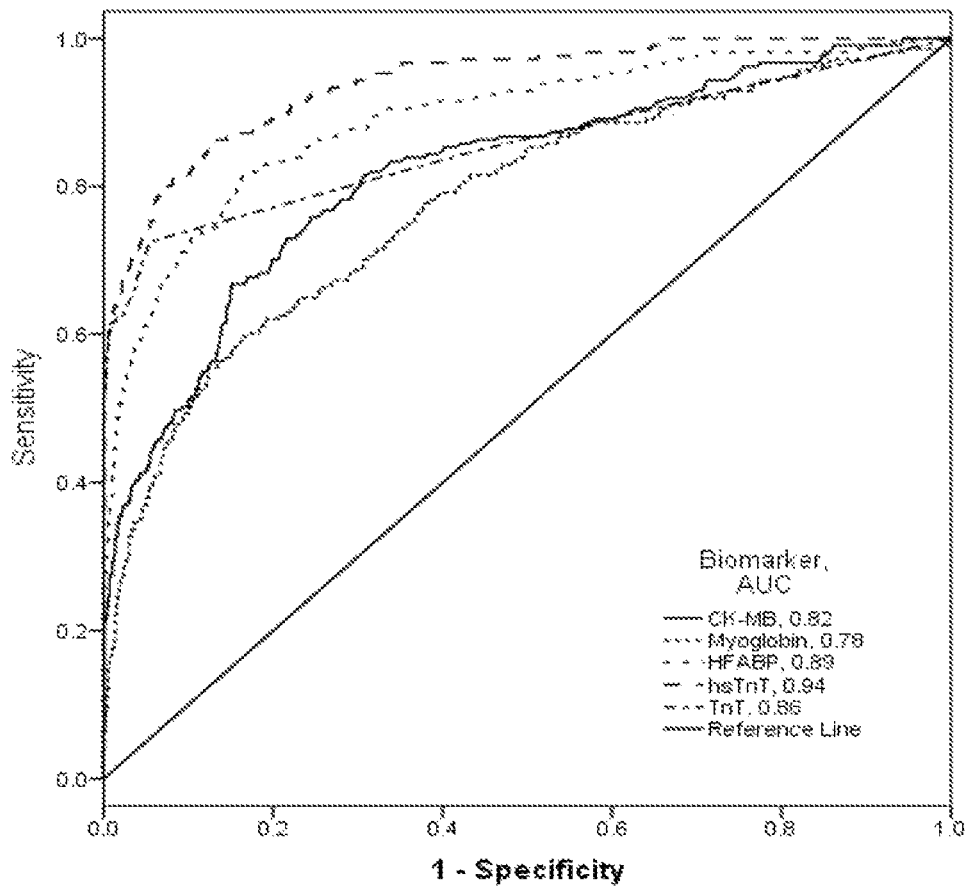
FIG. 1: Receiver operating characteristic (ROC) curves demonstrating the diagnostic performance of each biomarker for AMI.

Acute coronary syndrome (ACS) refers to a set of signs and symptoms usually a combination of chest pain and other features interpreted as being a result of abruptly decreased blood flow to the heart (cardiac ischemia). The subtypes of ACS include unstable angina (UA, not associated with heart muscle damage) and two forms of myocardial infarction (non-ST & ST elevated) in which heart muscle is damaged.

Acute myocardial infarction (AMI or MI), more commonly known as a heart attack, refers to a medical condition that occurs when the blood supply to a part of the heart is interrupted, most commonly due to rupture of a vulnerable plaque. The resulting ischemia (oxygen shortage) if left untreated for a sufficient period can cause damage and/or death to heart tissue.

H-FABP is present in the myocardium and is believed to be rapidly released into circulation as a result of myocardial injury. Numerous studies have demonstrated that it is an early marker for occurrence of MI. It will be understood to those skilled in the art that H-FABP incorporates any variant polypeptides which share the same essential biological and immunological properties as the specific H-FABP peptides used in the current invention.

The terms 'troponin' and 'cardiac troponin' as used by the current invention refer to all isoforms of troponin which are expressed in the cells of the heart, preferably they refer to cardiac troponin T or cardiac troponin I, most preferably cardiac troponin T.

The terms 'cardiac troponin level' and 'H-FABP level' refer to the concentration of cTnT and H-FABP respectively, preferably their concentration in a plasma or serum sample from a subject of the current invention. The 'reference values' or 'cut-off levels' used in the current invention are commonly acceptable levels of cTnT and H-FABP which are indicative of a recently occurring MI. Preferably for cTnT the reference value is based upon the $99^{th}$ percentile of a reference population as determined by the manufacturer. Preferably for H-FABP the reference value is based on the $95^{th}$ percentile of a reference population as determined by the manufacturer.

In the current invention the term 'ruling out' means excluding a diagnosis of myocardial infarction.

A subject of the current invention is an animal, more preferably a mammal, even more preferably a human. The subject is preferably one whom presents to an emergency department with chest pain but can refer to any suspected, assumed or possible ACS cases in which symptoms are present but no diagnosis has been established. The sample from said subjects of the current invention can be selected from a body fluid, separated cells or tissue sample. Most preferably the sample is a body fluid, even more preferably the sample is serum or plasma.

The combination of the current invention is characterised by a very high sensitivity and very high negative predictive value. A high sensitivity of 99.1% means that the current invention rarely misses an actual positive result and therefore a negative result should be reassuring. This is further supported by the combinations high negative predictive value (99.7%) which means that when the test yields a negative result it is most likely correct in its assessment.

In the context of the current invention the phrase 'positive ECG changes' refers to any deviation from a normal ECG which is associated with an acute myocardial infarction. This may include for example ST segment elevation or new onset left bundle branch block or ST segment depression or T wave inversion. The ECG is preferably a standard 12-lead ECG but any suitable variation known to those skilled in the art may be used to interpret the electrical activity of the heart.

A further embodiment of the current invention is a method for risk stratification of subjects testing positive for at least one of H-FABP, cTnT or ECG to predict the risk of a major adverse cardiac event occurring in said subject within 30 days of initial presentation. The term 'MACE' as used in the current invention is defined as AMI, death or the need for cardiac revascularization.

All publications cited herein are hereby incorporated by reference in their entirety.

Methods

Patient Group

We undertook a diagnostic cohort study, pooling prospectively collected data from two UK centres, Manchester Royal Infirmary, an inner city university affiliated teaching hospital and Stepping Hill Hospital, Stockport, a suburban District General Hospital in South Manchester. Several separate analyses using data from the Manchester cohort have been published (10-17). Ethical approval was obtained separately at each centre (references 05/Q1410/27 and 09/H1014/74) as the primary goal was to derive and validate a clinical decision rule. All participants provided written informed consent.

We included patients who presented to the ED with a primary complaint of chest pain that was suspected to be cardiac in nature. We excluded patients whose symptoms were secondary to trauma (and had suspected myocardial contusion), pregnant patients, those who were unable to speak English or lacked the capacity to provide written informed consent, patients with renal failure requiring dialysis, patients with another medical condition requiring hospital admission, prisoners and those who did not have an admission blood sample available for testing.

Sample Analysis

Participants underwent venepuncture at the time of presentation to the ED. Serum was frozen at $-70°$ C. pending subsequent testing. Heart fatty acid binding protein (H-FABP), creatine kinase MB (CK-MB) and myoglobin were measured using the cardiac plus array on the Evidence Investigator platform (Randox Laboratories Ltd, Crumlin, County Antrim, UK). Standard troponin T (TnT) and high sensitivity troponin T (hs-TnT) were both measured using the Elecsys array (Roche Diagnostics, Burgess Hill, West Sussex, UK). The diagnostic cut-offs for each biomarker, based on the $95^{th}$ percentile (unless stated) of a reference population as determined by the manufacturer, were H-FABP 2.5 µg/L; CK-MB 1.92 µg/L; myoglobin 66 µg/L; TnT $99^{th}$ percentile 10 ng/L (10% CV 35 ng/L); hs-TnT $99^{th}$ percentile 14 ng/L (10% CV 12 ng/L).

All patients underwent TnT testing at least 12 hours after symptom onset. The primary outcome was a diagnosis of AMI, which was adjudicated by two independent investigators who were blinded to investigational assay results. In accordance with the universal definition of myocardial infarction, AMI was defined as a rise and/or fall of troponin above the $99^{th}$ percentile in the appropriate clinical context.

The secondary outcome was the occurrence of major adverse cardiac events (MACE) within 30 days of initial presentation. MACE was defined as AMI, death or the need for coronary revascularization. Patients were followed up by telephone and electronic chart review. Where it was not possible to contact the patient, their general practitioner was contacted. Details of all hospitalisations and investigations were obtained.

Statistical Analysis

Data which were not normally distributed ($p<0.05$ on the Kolmogorov-Smirnov test) were summarised by the median and interquartile range (IQR); continuous data were compared using the Mann-Whitney U test. Dichotomous data were compared by chi-squared testing. The diagnostic performance of each biomarker was summarised by calculation of sensitivity, specificity, positive and negative predictive values (PPV and NPV respectively) and area under the receiver operating characteristic (ROC) curve (AUC, or C-statistic), each with 95% confidence intervals (95% CI). Multivariate analysis was undertaken using forward stepwise logistic regression ($p<0.05$ for entry, $p<0.1$ for removal). Variables entered into the model included hs-TnT, H-FABP, age, sex, CK-MB, myoglobin and ECG changes compatible with acute ischaemia. Biomarker levels were split into deciles for the purposes of this analysis. All statistical analyses were undertaken using SPSS version 19.0 (SPSS Inc, Chicago, Ill.) except for diagnostic test characteristics, which were calculated using MedCalc version 11.6.1.0 (MedCalc Software, Mariakerke, Belgium).

Results

A total of 1,171 participants were included: 698 patients from the Manchester cohort and 473 from Stockport (FIG. 1).

Figure 2:
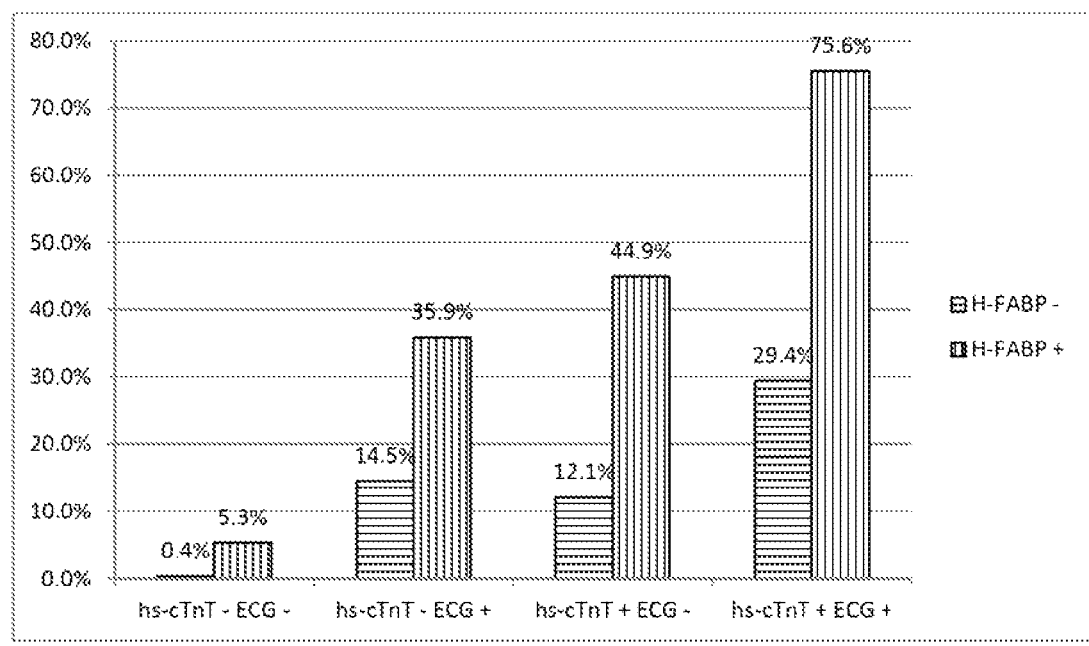
FIG. 2: Proportion of patients with AMI stratified by hs-TnT, H-FABP, and the presence or absence of ECG ischaemia at presentation.

Key baseline characteristics are shown in table 1. 212 (18.1%) patients were diagnosed with AMI. As shown in FIG. 2, the area under the ROC curve (AUC) for hs-TnT was 0.94 (95% CI 0.92-0.96). The corresponding AUC for H-FABP was 0.89 (95% CI 0.86-0.92). The sensitivity, specificity, PPV and NPV of each biomarker are shown in Table 2. The combination of H-FABP and TnT had a sensitivity of 92.9% (95% CI 88.6-96.0%), specificity 75.1% (72.2-77.8%), PPV 45.2% (40.4-50.0%) and NPV 98.0% (96.7-98.9%). This combination was significantly more sensitive than hs-TnT alone (absolute difference in sensitivity 4.3%, 95% CI 0.3-6.5%, p=0.0352) although specificity was lower (absolute difference 5.6%, 95% CI 2.9-8.2%, p=0.0001). H-FABP and hs-TnT had equivalent sensitivity up to 6 hours from symptom onset and hs-TnT had superior sensitivity at later time points.

Figure 3:
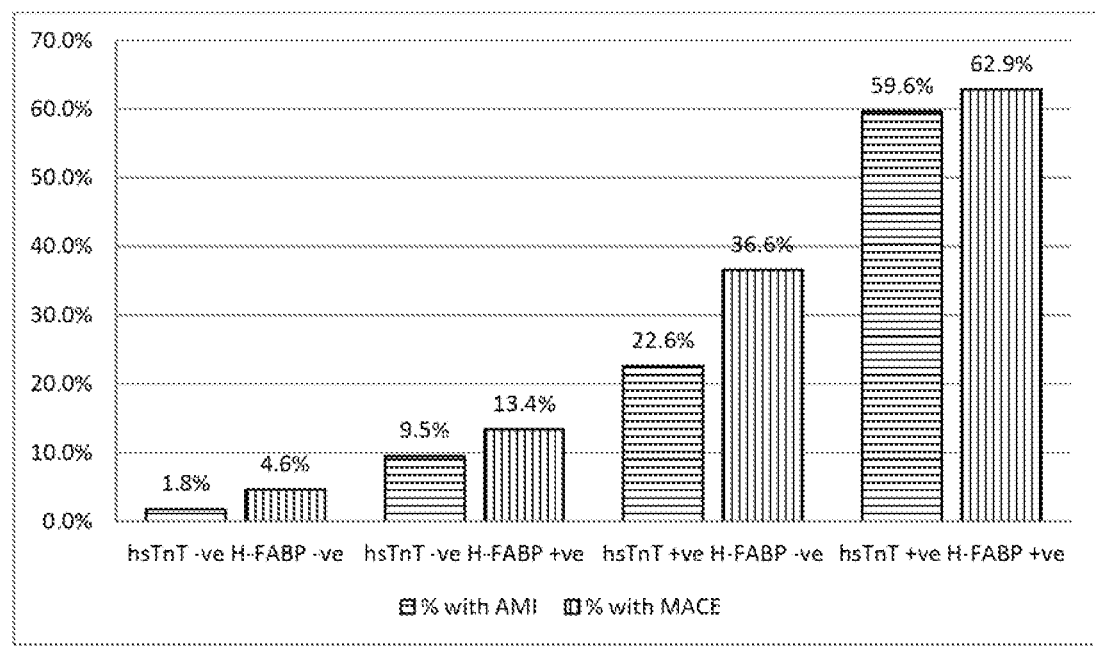
FIG. 3: Proportion of patients with AMI and MACE stratified by hs-TnT and H-FABP levels at presentation.

H-FABP had diagnostic value independent of hs-TnT and ECG findings (adjusted odds ratio 5.1, 95% CI 3.2-8.2, p<0.0001). This independent diagnostic value is demonstrated in FIG. 3. The combination of H-FABP and hs-TnT had a sensitivity of 94.3% (95% CI 90.3-97.0) and negative predictive value 98.2% (96.9-99.1%). With the combination of H-FABP, hs-TnT and ECG, sensitivity rose to 99.1% (95% CI 96.6-99.9%) and negative predictive value to 99.7% (98.7-100.0%). Specificity was 59.3% (56.2-62.5%) and positive predictive value 35.0% (31.2-39.0%). If AMI was considered to be excluded in patients with normal H-FABP, hs-TnT and ECG, AMI would be excluded in 48.8% of patients at a cost of missing 0.95% (n=2) AMIs. Both patients missed by the combination presented to the ED within 1 hour of symptoms and had small late troponin elevations (50 ng/L and 60 ng/L respectively). Both underwent in-patient coronary angiography. One patient had a tubular stenosis to the mid-left anterior descending artery, which required no intervention. The other had a significant circumflex stenosis, which was stented.

In addition to their diagnostic value, hs-TnT, H-FABP and the ECG carried independent prognostic value (for predicting MACE within 30 days). Even after accounting for hs-TnT and ischaemic ECG changes, HFABP had an adjusted odds ratio of 2.8 (95% CI 1.9-4.2, p<0.0001) for predicting MACE.

Clinical Applications of the Invention
  i) On presentation to the emergency department a biological sample can be taken from a patient displaying ACS like symptoms and tested for the biomarkers of the invention (H-FABP and hs-TnT), which in combination with an ECG allow for safe and immediate exclusion of AMI, thus avoiding the need for serial sampling and hospital admission for many patients.
  ii) The invention also enables stratification of the remaining patients into risk groups. Positivity for all three investigations identifies a population at extremely high risk of a MACE within 30 days (75.6%). Patients with positive hs-TnT and ischaemic ECG changes but negative H-FABP have a risk of only 29.6%. Clearly, the former group would warrant closer observation and are more likely to benefit from more intensive anti-platelet treatment than the latter.

I claim:

1. A method for 'ruling out' acute myocardial infarction (AMI) in a subject presenting with chest pain expected to be cardiac in nature, the method comprising:
    a) recording an Electrocardiography (ECG) reading from said subject,
    b) determining the amount of Heart-type Fatty acid binding protein (H-FABP) and cardiac Troponin T (cTnT) in a sample from said subject,
    c) comparing the results from b) to reference values for ruling out an acute Myocardial Infarction in a subject, wherein the reference value for H-FABP for ruling out a myocardial infarction is 2.5 ng/ml and a H-FABP value below this reference value indicates that a recent AMI has not occurred, and
    d) based on the results from steps a)-c) either 'ruling out' or 'ruling in' a diagnosis of acute Myocardial Infarction in said subject.

2. The method of claim 1 wherein the reference value for cTnT for ruling out a myocardial infarction is 0.014 ng/ml and a cTnT value below this reference value indicates that a recent AMI has not occurred.

3. The method of claim 1 in which the cTnT assay is a high sensitive cTnT assay.

4. The method of claim 2 in which the cTnT assay is a high sensitive cTnT assay.

5. The method of claims 1 wherein the sample is whole blood, serum or plasma.

6. The method of claim 1 in which a single blood draw is made from the subject at the time of presentation.

7. The method of claims 2 in which a single blood draw is made from the subject at the time of presentation.

8. The method of claims 3 in which a single blood draw is made from the subject at the time of presentation.

9. The method of claim 4 in which a single blood draw is made from the subject at the time of presentation.

10. A method for risk stratification of subjects testing positive for at least one of H-FABP, cTnT or ECG in claim 1 to predict the risk of a major adverse cardiac event occurring in said subject within 30 days of initial presentation.

11. The method of claim 10 wherein a subject is placed into a high risk group if said subject has a cTnT value above a reference value for ruling out AMI, has positive ECG changes and also an H-FABP value above a reference value for ruling out AMI.

12. The method of claim 10 wherein a subject is placed into a lower risk group if said subject has a cTnT value above a reference value for ruling out AMI and has positive ECG changes but with an H-FABP value below a reference value for ruling in AMI.

* * * * *